US012770733B2

(12) United States Patent
Parkinson et al.

(10) Patent No.: US 12,770,733 B2
(45) Date of Patent: Oct. 20, 2026

(54) HEALTH MONITORING SYSTEM

(71) Applicant: Reset Health Clinics Limited, London (GB)

(72) Inventors: Jay Parkinson, London (GB); Andrew Liles, London (GB); Grant Harrison, London (GB); David Wong, London (GB)

(73) Assignee: Reset Health Clinic Limited, London (GB)

( * ) Notice: Subject to any disclaimer, the term of this patent is extended or adjusted under 35 U.S.C. 154(b) by 0 days.

(21) Appl. No.: 18/846,306

(22) PCT Filed: Mar. 14, 2023

(86) PCT No.: PCT/GB2023/050599
§ 371 (c)(1),
(2) Date: Sep. 12, 2024

(87) PCT Pub. No.: WO2023/175318
PCT Pub. Date: Sep. 21, 2023

(65) Prior Publication Data
US 2025/0201400 A1 Jun. 19, 2025

(30) Foreign Application Priority Data
Mar. 16, 2022 (GB) ...................................... 2203626

(51) Int. Cl.
*G16H 40/67* (2018.01)
*G16H 10/20* (2018.01)
(Continued)

(52) U.S. Cl.
CPC ............. *G16H 40/67* (2018.01); *G16H 10/20* (2018.01); *G16H 20/00* (2018.01); *G16H 70/20* (2018.01); *G16H 80/00* (2018.01)

(58) Field of Classification Search
CPC ........ G16H 40/67; G16H 10/20; G16H 20/00; G16H 70/20; G16H 80/00; G16H 10/60; G16H 40/20
See application file for complete search history.

(56) References Cited

U.S. PATENT DOCUMENTS

2015/0112703 A1* 4/2015 Sysko .................... G16H 20/13 705/2
2021/0142903 A1* 5/2021 Mason ................... G16H 20/30

FOREIGN PATENT DOCUMENTS

WO 2021/087320 A1 5/2021
WO WO-2021236702 A1 * 11/2021 ............. G16H 70/60

OTHER PUBLICATIONS

Jun. 26, 2023 (WO) International Search Report and Written Opinion—App PCT/GB2023/050599.

* cited by examiner

*Primary Examiner* — Chinyere Mpamugo
(74) *Attorney, Agent, or Firm* — KellDann Law PLLC

(57) ABSTRACT

An automated system and computer implemented method for providing medical health care services to a remote patient, the system comprising a memory, a datastore, a communication component, and a processor coupled to the memory and configured to transmit to a first remote device using the communication component, a first set of queries. Receive from the first remote device using the communication component and in response to the first set of queries, first response data. Store in the data store, the set of queries and responses to the one or more queries and a health condition associated with a first user of the remote device. Determine a second set of queries, different to the first set of queries, based on the response received from the first remote device. Transmit using the communication component to a second device having a second user with the same health
(Continued)

condition as the first user, the second set of queries. Receive from the second remote device using the communication component and in response to the second set of queries, second response data. Generate a treatment plan for the health condition based on the second response data. Transmit to the second device, using the communication component, the treatment plan.

20 Claims, 11 Drawing Sheets

(51) Int. Cl.

| | |
|---|---|
| ***G16H 20/00*** | (2018.01) |
| ***G16H 70/20*** | (2018.01) |
| ***G16H 80/00*** | (2018.01) |

HEALTH MONITORING SYSTEM

CROSS REFERENCE TO RELATED APPLICATIONS

This application is a national stage application under 35 U.S.C. § 371 of PCT/GB2023/050599, filed on Mar. 14, 2023, entitled "Remote Health Monitoring System Comprising Artificial Intelligence", which claims the benefit of British Patent Application No. 2203626.3, filed Mar. 16, 2022, each of which is incorporated herein by reference in its entirety.

FIELD OF THE INVENTION

The present invention relates to a health monitoring system and method and in particular, an automated health monitoring system and method.

BACKGROUND OF THE INVENTION

The provision of health care services requires many years of training and must be applied in a careful and monitored manner. Medical health care services can be provided in different ways. Health care services can be provided more efficiently using remote technologies such as video calls and electronic messaging systems. These remote systems also have the benefit of avoiding the transmission of contagious diseases between doctor and patient. However, these systems tend to rely on a clinician or medical practitioner applying their own expertise to a particular patient presenting with one or more conditions. Whilst high quality healthcare can be provided in this way, outcomes may vary according to the particular skills and experience of each individual health practitioner and the types of patients that they treat.

Some level of automation can be achieved for certain regular health care tasks, such as the preparation of doctor's orders (prescriptions) but a level of manual intervention and monitoring is still required from a health professional, such as a doctor.

Therefore, there is required a method and system that overcomes these problems.

SUMMARY OF THE INVENTION

The system includes a communication interface used to communicate with remote devices (e.g., smartphones, tablet computers, desktop computers, etc.). Queries, questions or requests for information are sent to a first remote device. These queries are sent in order to obtain information about a health condition of a user of the first remote device. However, the queries need not always be directly relevant to the particular health condition. The queries are stored in a database or other datastore and associated with the health condition of the user.

The user responds, using their remote device. These responses may also be stored and associated with the health condition and/or user. The responses may be received by the system using the communication interface. Another second user may have the same or a similar health condition. At some time after the responses are received from the first user, a further set of queries are devised. These may have one or more queries in common with the first set or be completely different queries. The first set of queries and their responses are used to determine the second set of queries. For example, if any of the first queries can't be answered or if the answers prompt additional questions, then these can be included in (or removed from) the second set of queries. Therefore, as queries and responses are sent to different users then the sets of queries can improve, especially if there are trends that are common between different users with similar health conditions.

Treatment plans are generated based on the responses, which are sent to the remote devices. The further set of queries may be based on one or more earlier or previous sets of queries and/or their responses. Optionally, tests may be ordered based on the responses. The results of the tests may also be used to devise future query sets or other tests sent to patients. Improved and personalised treatment plans may be generated in this way.

Preferably, the system may iterate the steps with improvements in the sets of queries occurring for each iteration or over time. In other words, the first sets of queries can be considered as earlier sets of queries in an iteration and the second sets of queries can be considered later sets of queries in an iteration with responses being received in between. In this way, the sets of queries (and treatment plans and optionally sets of tests) can evolve and improve as the system operates and more data are collected. The earlier sets of queries in a particular iteration may be derived from (or identical to) the later sets of queries from an earlier (or the preceding) iteration.

In accordance with a first aspect there is provided an automated system for providing medical health care services to a remote patient, the system comprising:

a memory;

a datastore;

a communication component; and a processor coupled to the memory and configured to:

transmit to a first remote device using the communication component, a first set of queries;

receive from the first remote device using the communication component and in response to the first set of queries, first response data;

store in the data store, the set of queries and responses to the one or more queries and a health condition associated with a first user of the remote device;

determine a second set of queries, different to the first set of queries, based on the response received from the first remote device;

transmit using the communication component to a second device having a second user with the same health condition as the first user, the second set of queries;

receive from the second remote device using the communication component and in response to the second set of queries, second response data;

generate a treatment plan for the health condition based on the second response data; and transmit to the second device, using the communication component, the treatment plan. Therefore, an improved set of queries can be devised automatically leading to improvements and efficiencies. Irrelevant queries can be filtered out automatically and new queries can be added so that overall, fewer responses are required to provide the right treatment. Furthermore, improved treatment plans can be derived quicker.

Preferably, the health monitoring system may further comprise an artificial intelligence (AI) component trained using the data in the datastore and configured to determine the second set of queries and/or the treatment plan. The AI component can be trained over time with real data leading to an improved model.

Optionally, the datastore may contain historical treatment plans, queries transmitted to users of remote devices, responses to the queries transmitted to the users of remote devices and associated health conditions. These data can be used to further improve new query sets for users having the same or similar health conditions. These data may also be used by the AI component.

Optionally, the treatment plan may include any one or more of: a medication prescription; a lifestyle variation; a diet instruction; an exercise instruction; and a physiotherapy prescription. The treatment plan may include other details and information.

Optionally, the processor may be further configured to (e.g., by computer readable instructions stored in the memory):

generate a medical test plan including one or more medical tests when determining the second set of queries;

receive results from the one or more medical test; and generate the treatment plan based on the second response data and the results of the one or more medical tests results. Therefore, the overall treatment process may be managed more efficiently.

Optionally, the one or more medical tests may include any one or more of: a blood test; an X-ray investigation; an MRI investigation; a CT scan investigation; and a fitness test. Tests may also involve the assessment of physical flexibility, physiological change, psychological change, and/or memory or alertness improvement. Other tests or test types may be included.

Optionally, generating the medical test plan may further comprise using results of one or more medical tests of a medical test plan sent to the first remote device. Therefore, information from multiple users with similar health conditions can be used to devise more effective medical test plans.

Optionally, the memory may be further configured to store the second set of results in the data store.

Optionally, the memory is further configured to:

change the first set of queries based on the response received from the first remote device and/or the second remote device;

transmit to a first remote device using the communication component, the changed first set of queries;

receive from the first remote device using the communication component and in response to the changed first set of queries, third response data;

generate a treatment plan based on the third response data; and transmit to the first device, using the communication component, the treatment plan generated based on the third response data. Therefore, further improvements in effectiveness and efficiencies may be made.

Optionally, the health condition may be any one or more of: diabetes; heart disease; obesity; and hypertension. Any and other health conditions may be included. The health condition may include any particular combinations of two or more health conditions, which may be more difficult to treat than individual health conditions.

Optionally, the queries forming the sets of queries may be selected from queries stored within the data store. The stored query sets (e.g., associated with particular health conditions or combinations of health conditions) may be updated as more data are collected.

Preferably, the processor (e.g., using instructions stored in the memory) may be further configured to:

generate new queries based on received responses to first and/or second sets of queries; and store the generated new queries in the datastore for use as further query sets to be sent to one or more remote devices.

Advantageously, the processor (e.g., using instructions stored in the memory) may be further configured to:

receive a success criteria related to the health condition; and determine, based on the received responses to first and/or second sets of queries, progress towards the success criteria.

Optionally, the processor (e.g., using instructions stored in the memory) may be further configured to:

determine, based on the received responses to first and/or second sets of queries, an expected time for a user of the remote device to reach meet the success criteria for their health condition. The expected time may be updated as more data are collected. The expected time may be based on data collected for other users having similar health conditions or sets of health conditions, for example. Furthermore, the stored data may be used to predict outcomes for patients. For example, probabilities may be calculated based on historical and stored data.

Optionally, the second set of queries and the treatment plan may be stored as a template set of queries and a template treatment plan in the data store.

Optionally the processor (e.g., using instructions stored in the memory) may be further configured to:

update the template set of queries and template treatment plan based on further received responses to queries. The system and method may iterate for a number of iterations or indefinitely.

Preferably, the health monitoring system may further comprise a natural language processor configured to process the responses and/or the queries. Therefore, the system may automatically obtain data from human queries and responses. The system may interpret one or more languages in this this way.

Optionally, the processor (e.g., using instructions stored in the memory) may be further configured to:

generate a treatment plan for the health condition based on the first response data; and transmit to the first device, using the communication component, the treatment plan.

In accordance with a second aspect, there is provided a computer implemented method for providing automated medical health care services to a remote patient, the method comprising the steps of:

transmitting to a first remote device using the communication component, a first set of queries;

receiving from the first remote device using the communication component and in response to the first set of queries, first response data;

storing in the data store, the set of queries and responses to the one or more queries and a health condition associated with a first user of the remote device;

determining a second set of queries, different to the first set of queries, based on the response received from the first remote device;

transmitting using the communication component to a second device having a second user with the same health condition as the first user, the second set of queries;

receiving from the second remote device using the communication component and in response to the second set of queries, second response data;

generating a treatment plan for the health condition based on the second response data; and transmitting to the second device, using the communication component, the treatment plan.

The computer implemented method may further comprise iterating the steps to generate a further second set of queries based on further first response data and a further treatment plan based on further second response data at each iteration. All steps may be iterated or looped. This may continue indefinitely, with the determined second sets of queries being used as the first sets of queries on the next or subsequent iteration. The queries and responses may be stored in the data store for use in further analysis and improvement.

The methods described above may be implemented as a computer program comprising program instructions to operate a computer. The computer program may be stored on a computer-readable medium.

The computer system may include a processor or processors (e.g. local, virtual or cloud-based) such as a Central Processing unit (CPU), and/or a single or a collection of Graphics Processing Units (GPUs). The processor may execute logic in the form of a software program. The computer system may include a memory including volatile and non-volatile storage medium. A computer-readable medium may be included to store the logic or program instructions. The different parts of the system may be connected using a network (e.g. wireless networks and wired networks). The computer system may include one or more interfaces. The computer system may contain a suitable operating system such as UNIX, Windows® or may be a Container host, for example.

It should be noted that any feature described above may be used with any particular aspect or embodiment of the invention.

BRIEF DESCRIPTION OF THE FIGURES

The present invention may be put into practice in a number of ways and embodiments will now be described by way of example only and with reference to the accompanying drawings, in which.

It should be noted that the figures are illustrated for simplicity and are not necessarily drawn to scale. Like features are provided with the same reference numerals.

DETAILED DESCRIPTION OF THE PREFERRED EMBODIMENTS

Figure 1:
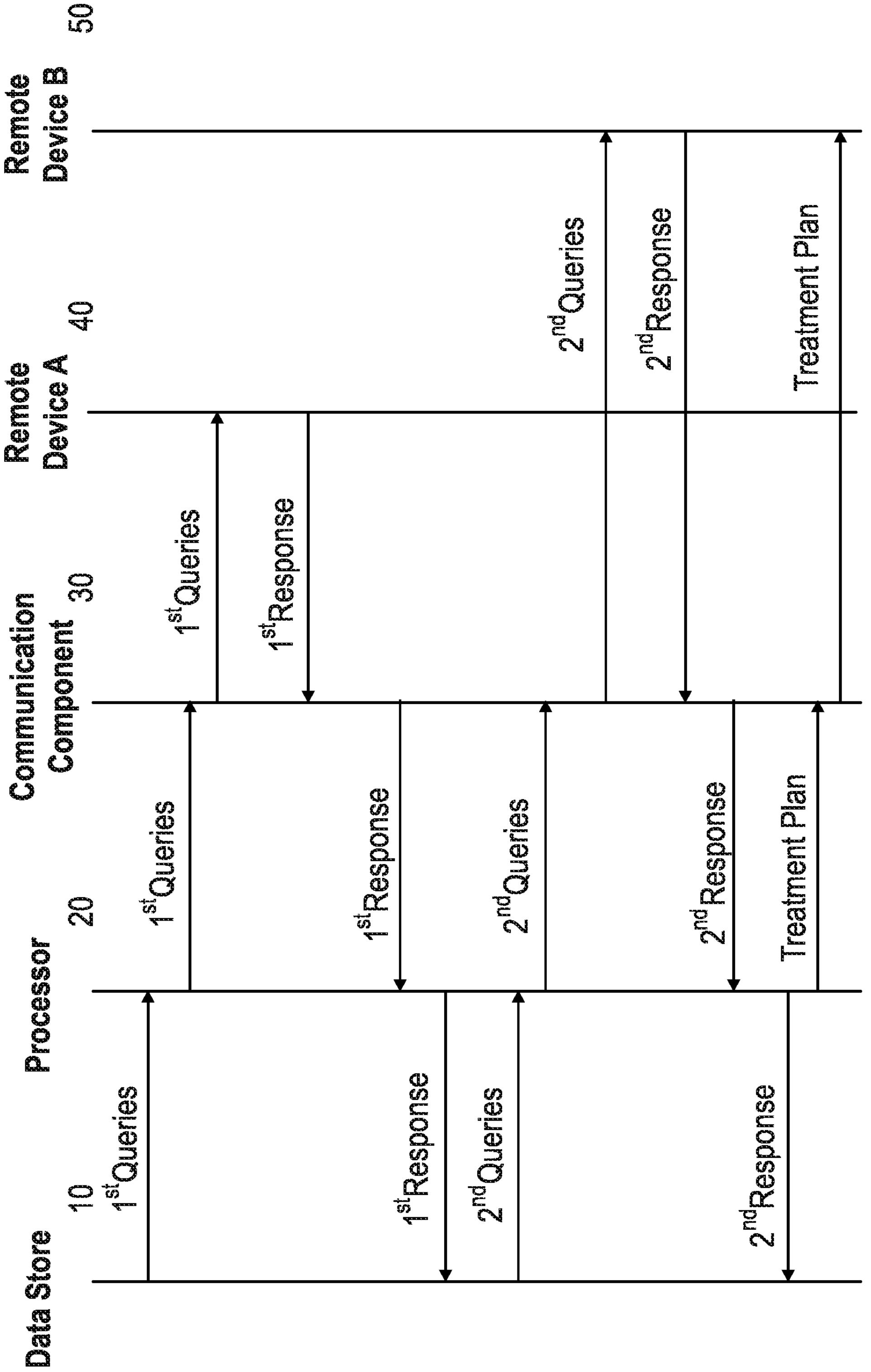
FIG. 1 shows a sequence diagram of a method for providing health care services to a remote patient, given by way of example only.

FIG. 1 shows a sequence diagram illustrating a method for providing health care services. The interacting components include a data store 10, a processor 20, a communication component 30, remote device A 40 and remote device B 50.

The processor 20 generates or receives a first set of queries and transmits this first set of queries to remote device A 40 via the communication component 30. Communication component 30 may form a part of processor 20 or be separate from it. The first set of queries are stored in data store 10.

In response to the first set of queries, remote device A 40 sends a first set of responses to the processor 20 via the communication component 30. This may be sent (preferably securely) over the internet. This first set of responses are stored in the data store 10. The first sets of queries and responses are associated with a particular health condition within the data store 10. The first sets of queries and responses may also be associated with the user (member or patient) that was sent the queries.

The processor 20 uses the first set of responses (or one or more previous sets of responses) to determine a second set of queries, different to the first set of queries, to send to remote device B 50. The second set of queries may be retrieved from the data store 10 or generated by the processor 20. The first set of queries may also be used to determine the second set of queries. The users of remote devices A and B have the same or a similar health condition and these users provide inputs to remote devices A and B, which form the responses.

After the remote device B 50 sends the second set of responses to the processor 20, via communication component 30, the processor 20 generates a treatment plan for the health condition. This treatment plan is based on the responses to the second set of queries. This treatment plan is sent to remote device B 50 via the communication component 30. Preferably, the first and second responses may be stored in the data store 10 in order to accumulate data over time. These data can be used to enhance operation of the system 100.

This process shows at a high level, the steps used to devise the treatment plan based on responses to a more optimised set of queries. A treatment plan may also be sent to remote device A 40 based on the responses to the first set of queries provided by the user of this remote device. Template treatment plans for particular health conditions may be used. These template treatment plans may be stored within the data store 10. As responses are received from one or more members (patients) then these template treatment plans may be updated as data are collected. Treatment plans may include one or more items. For example, a treatment plan may include any one or more of: a medication prescription; a lifestyle variation; a diet instruction; an exercise instruction; and a physiotherapy prescription. The system may include components or functionality for communicating with remote systems. For example, the system may generate a treatment plan including a medication prescription (e.g., doctor's orders) and send this medication prescription (e.g., over a network such as the internet) to a pharmacy for filling. The member (patient) may then pick up this medication or receive it as a delivery to their home. The system can monitor whether or not the medication prescription was picked up (or received) by the patient.

Figure 2:
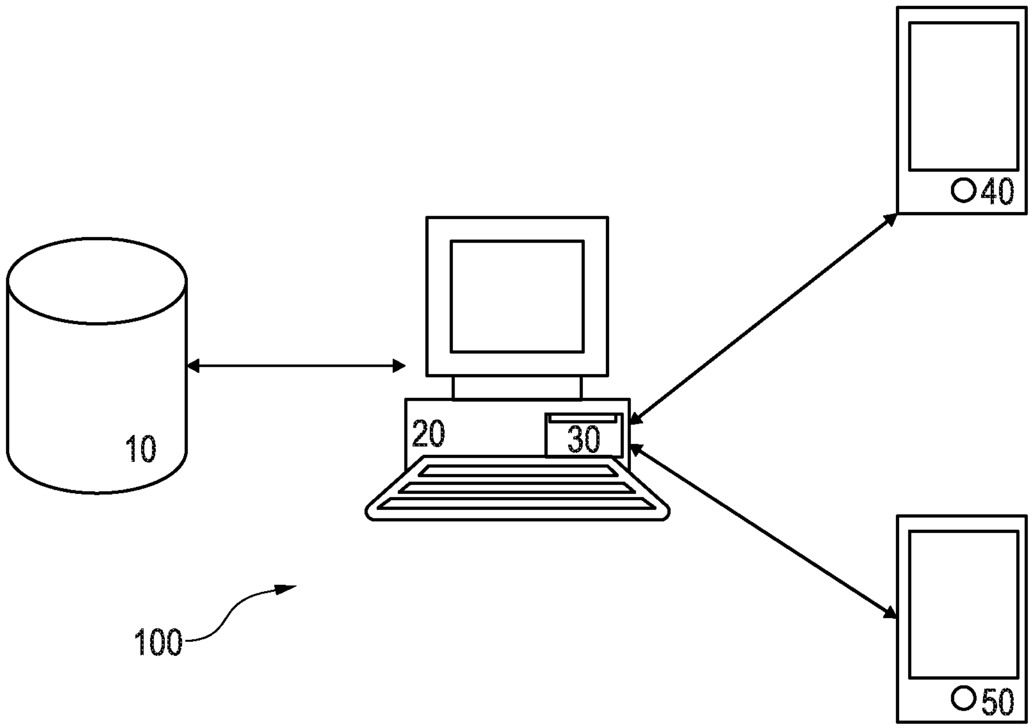
FIG. 2 shows a schematic diagram of a system for providing health care services to a remote patient.

FIG. 2 shows a schematic diagram of an automated system 100 for providing medical health care services to a remote patient. The system 100 incorporates the same components described with reference to FIG. 1. The system 100 may include further components that are not shown in this figure. FIG. 2 shows the processor (e.g., a server, virtual server, computer system, CPU or other computer) in communication with the data store 10 (e.g., a database, file system or distributed data storage). The data store 10 may form part of the same apparatus as the processor 20 or may be separate from it, as shown in FIG. 2. The processor 20 may be a physical server or a virtual server located remotely. The data store 10 may also be remote or virtual.

The communication component 30 is shown in FIG. 2 as being part of the same apparatus forming the processor 20. The communication component 30 may be any suitable interface (or series of interfaces) used to enable remote communication with remote device A 40 and remote device B50. For example, the communication component 30 may be a modem, router, wireless or wired interface with the internet, VPN, or cellular interface. Furthermore, additional remote devices (not shown in this figure) may also be in communication with the processor via the communication component 30. The communications may be secured using authentication and cryptographic techniques, for example.

The remote devices 40, 50 may be smartphones, laptop computers, tablet computers or other personal computing device that have communications capabilities (e.g., for communicating with the internet or other communications network such as a cellular network).

Other components that may be included in the system 100 include: a content management component; a messaging component; a project management component; and an artificial intelligence (AI) component.

The content management component may be used to create, store and edit content (including the queries), format messages, and generate templates and treatment plans. The messaging component can generate messages (including any content or queries) and send these to the communication component 30 for transmission. The project management component may administer, create and amend other components and add or change functionality of the system. The AI component can generate and enhance machine learning models based on stored data.

In order to evaluate the most optimal treatment plan for a new patient, the system may periodically recompute a Machine Learning model based on the previously accumulated queries, response, treatment plans together with a clinician-determined measurements of efficacy. The system learns which combination of inputs produced the observed outcomes and therefore be able to propose a treatment plan for a new patient.

The Machine Learnt model can continually be re-evaluated in light on new data that are received. An artificial intelligence (AI) component of the processor 20 may carry out this functionality. The AI component may have direct and real-time access to the data store 10 in order to use the collected data as training data (either supervised or unsupervised). The AI component may also be used to generate and update query sets based on previous queries sent to users (members/patients) and/or previous responses.

The system 100 may use machine learning to cluster like subjects together (e.g., to discover co-relations in data sets); and/or learn outcomes so that the system 100 can then predict categories or predict outcomes for the subject or other users. The nature of this kind of artificial intelligence is to produce true personalised analysis/predictions, rather than gross segmentation.

The following describes an example implementation of the system and method. Further enhancements are described. Any of the features and components that are described may be used with any other component in any particular combination Three different user types can interact with the system. Members (e.g., patients), Clinicians (e.g., health care workers, doctors, nurses, clinical psychologists, physiotherapists, dietician, etc.), and Mentors. Mentors may also be Members and can provide support to other Members.

A queue includes new activities ("action items"). These actions items come from Members that Clinicians are responsible for. These action items appear on the Clinician Queue.

Clinicians act as a team and they form a Pod. A Pod is a group of at least three Clinicians who work as a team. Pods exist so Clinicians can cross-cover one another when other Clinicians in the Pod are sick, on vacation, or any other reason why they wouldn't be able to respond in a timely manner. The Queue shows all Clinicians in a Pod. Activity from Members assigned to particular Clinicians are shown in The Queue as well as activity from Members that are assigned to other Clinicians the same Pod.

Members are assigned to a primary Clinician. New candidate Members are unassigned because those candidates have not yet interacted with a Clinician as this is the first action item they've created in the system.

New action items are organized by those assigned to a particular Clinician, unassigned, and assigned to others in the same Pod.

Information for each Action Item may include:

A condition (health condition) that this new activity relates to.

An activity type (e.g., new message, new Questions answered, etc.).

Whether or not the new action item is claimed by the Clinician viewing The Queue or another Clinician.

How long the action item has been in the Queue.

Action Items are new action items landing on a user's Queue that originate from either new messages created by Members or a Member interacting with an established Card. Every type of Card has very specific action items that can be created when a Member interacts with the Card. Action items that can be placed on the Queue may be defined in advance. This ensures a Clinician must actively take action to clear an action item from the Queue to ensure no action items are missed.

In order to avoid two Clinicians working on the same action item, Clinicians may "claim" an action item to put the action item into a state that prohibits other Clinicians from attempting to spend their time on that particular action item. Claiming an action item signals to other Clinicians "Hey I'm working this, don't also spend your time working something I'm working on." Also, "claiming" marks an action item(s) as "clear this action item(s) from the Queue via this next Stack I send to the Member." This concept of "claiming and sending" is what removes the action item from the Queue. Clinicians can also remove an action item from the Queue without sending a message or stack by "resolving" the action item. This is helpful for messages from Members that simply say something like "Thanks Doc!" Clinicians claim or resolve action items within messages or Cards in a Channel.

In order to speed up processing of action items within the Queue, these action items can be arranged by wait time. Therefore, the oldest action items will be found at the top of the Queue. However, Clinicians can also triage their Queue and prioritize those action items that may be more time sensitive than others.

Clinician teams evolve a close working relationship. They will be communicating closely about their hour-by-hour situation. When one Clinician is going off shift for example, they will communicate that to the rest of their team. This lets other Clinician team members know that they can claim action items on another team member's Queue.

A goal for the Queue for an individual Clinician and for their team is to have zero action items on their Queue because they've handled all incoming items in a timely way.

Figure 3:
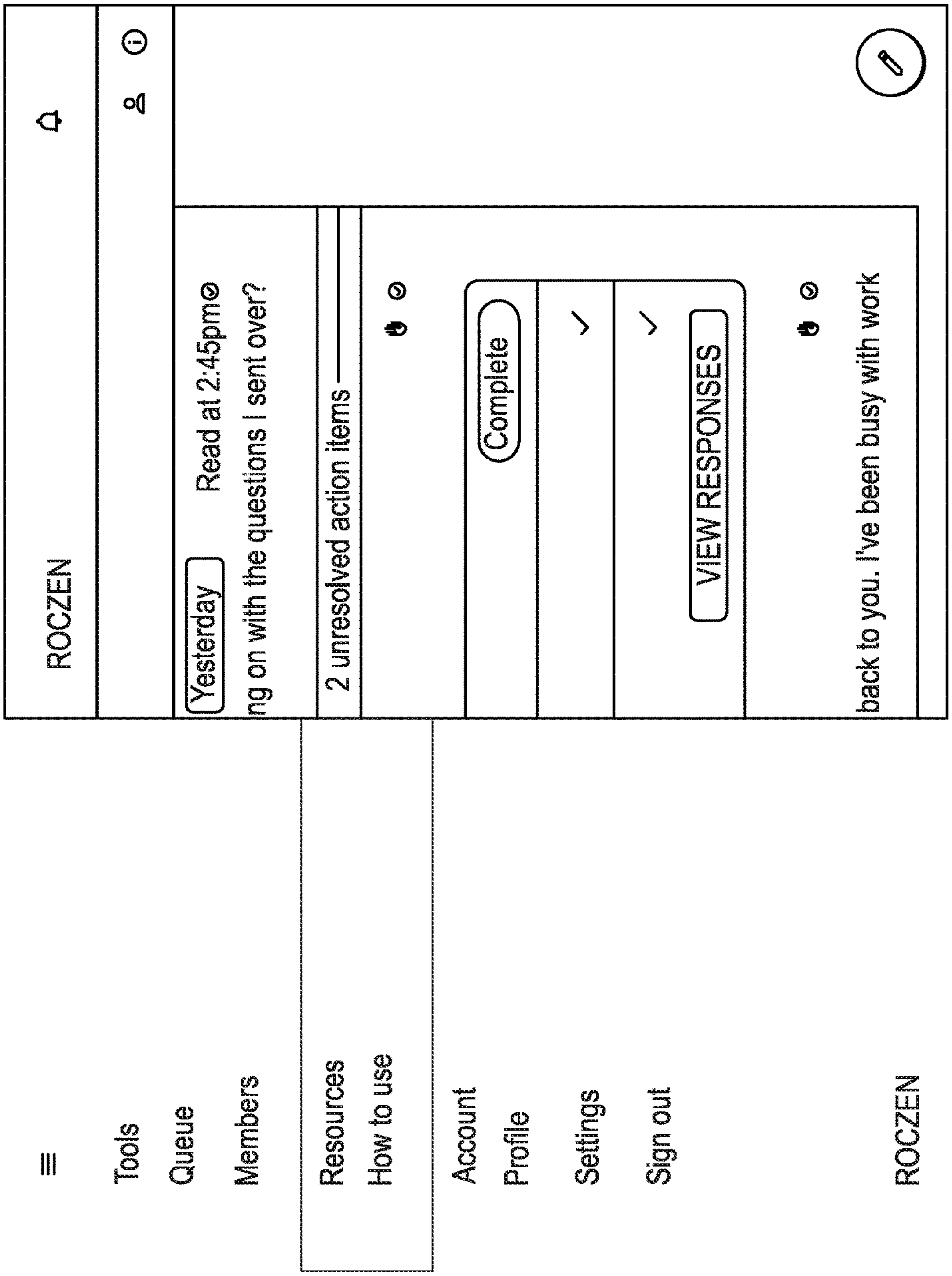
FIG. 3 shows a screen shot of a portion of the system of FIG. 2, including a navigation facility for a clinician.
Figure 4:
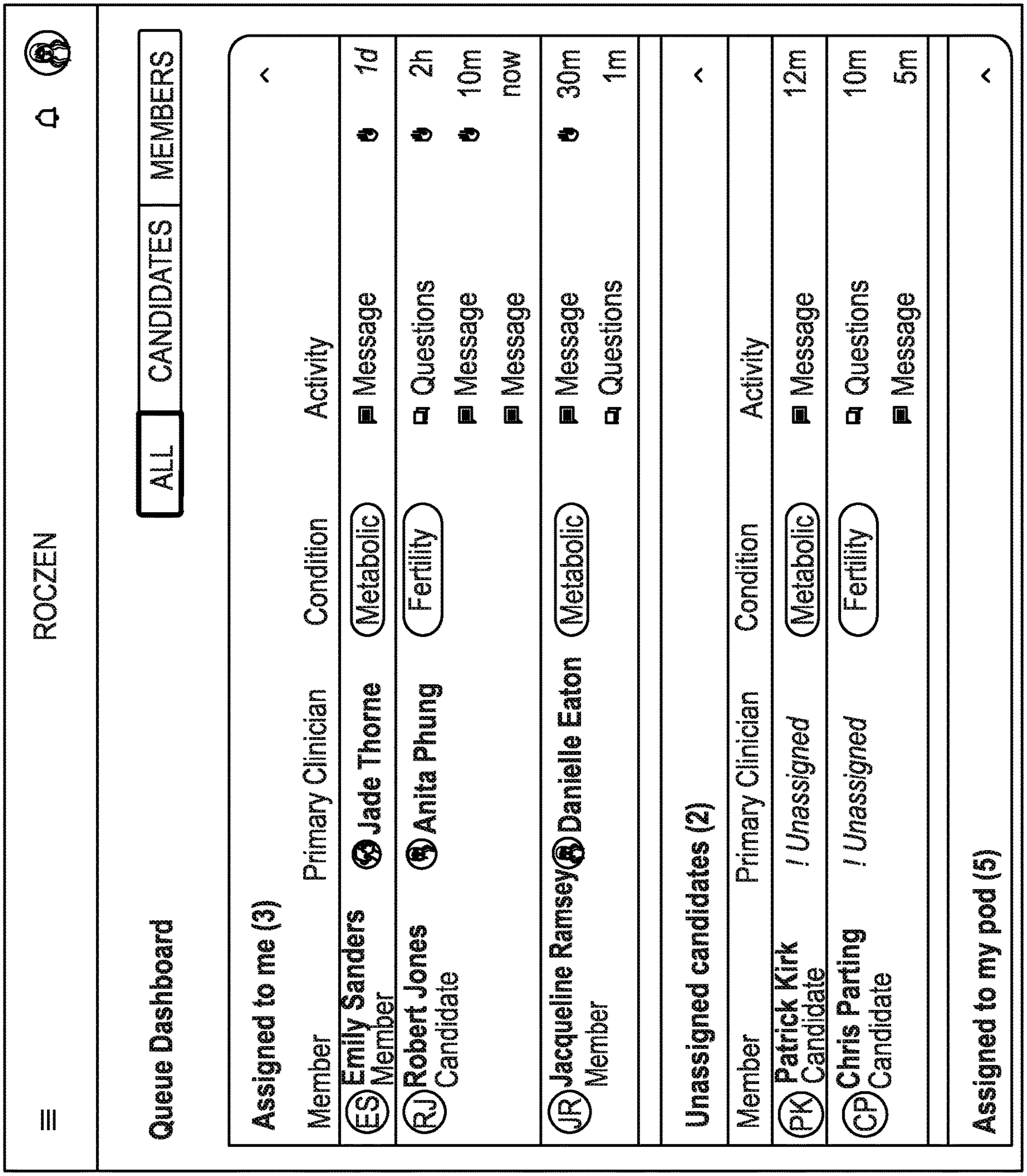
FIG. 4 shows a screen shot of a portion of the system of FIG. 2, including a clinician's view of a queue of actions.

FIGS. 3 to 11 show screen shots of a user interface for the various users of the system. FIG. 3 shows an example navigation screen for a Clinician. Clinicians can navigate anywhere in the platform via the navigation icon on the upper left side of their screen. FIG. 4 shows the Clinician view of the Queue. This includes Member details, their health conditions and particular activities that require attention.

A Clinician view of a Member Channel (not shown) may also be provided. The Member Channel is the thread of communication between Clinicians on the Pod and a Member. The information is contained within messages and "Cards." Cards are mini-apps that appears within a channel. These small applications may include automated responses and prompts for further information or responses. Cards can have "calls to action" and by clicking into a card, the Member can interact with the Card in different ways. For example, a Card may be a Question Card. By launching the Question Card, the Member can answer a series of questions, much like answering an online survey. This can form the basis of their responses to queries issued by the system 100.

A Clinician can access a screen having an overview of the Clinician/Member Channel. Over time, a channel may include all communications, all cards, and all clinical data about a specific condition that the system manages. The channel overview can become a summary of all the important information within that channel so Clinicians can easily find and digest the most important information within that channel. A Channel Info screen (not shown) can also provide a brief overview of Member Profiles and any incomplete action items in the Channel that a Clinician is responsible for.

As data is gathered by the system, more Cards may be developed. For example, a Clinician may send a message, attach a customized Question Card, and also send a Recipe Card to a Member (other cards may be generated). Clinicians can do this in a Stack Editor screen (not shown) by creating a Message, adding a Question Card, and adding a Recipe Card. A Stack of Cards can be sent to one or more Members. Stacking Cards reduces the number of communications required by the system and may also reduce the number notifications that Members receives, whilst gathering all necessary information. When creating a Stack, a Clinician can review the entire channel thread on the left side of their screen so that they can consume and create content at the same time.

Figure 5:
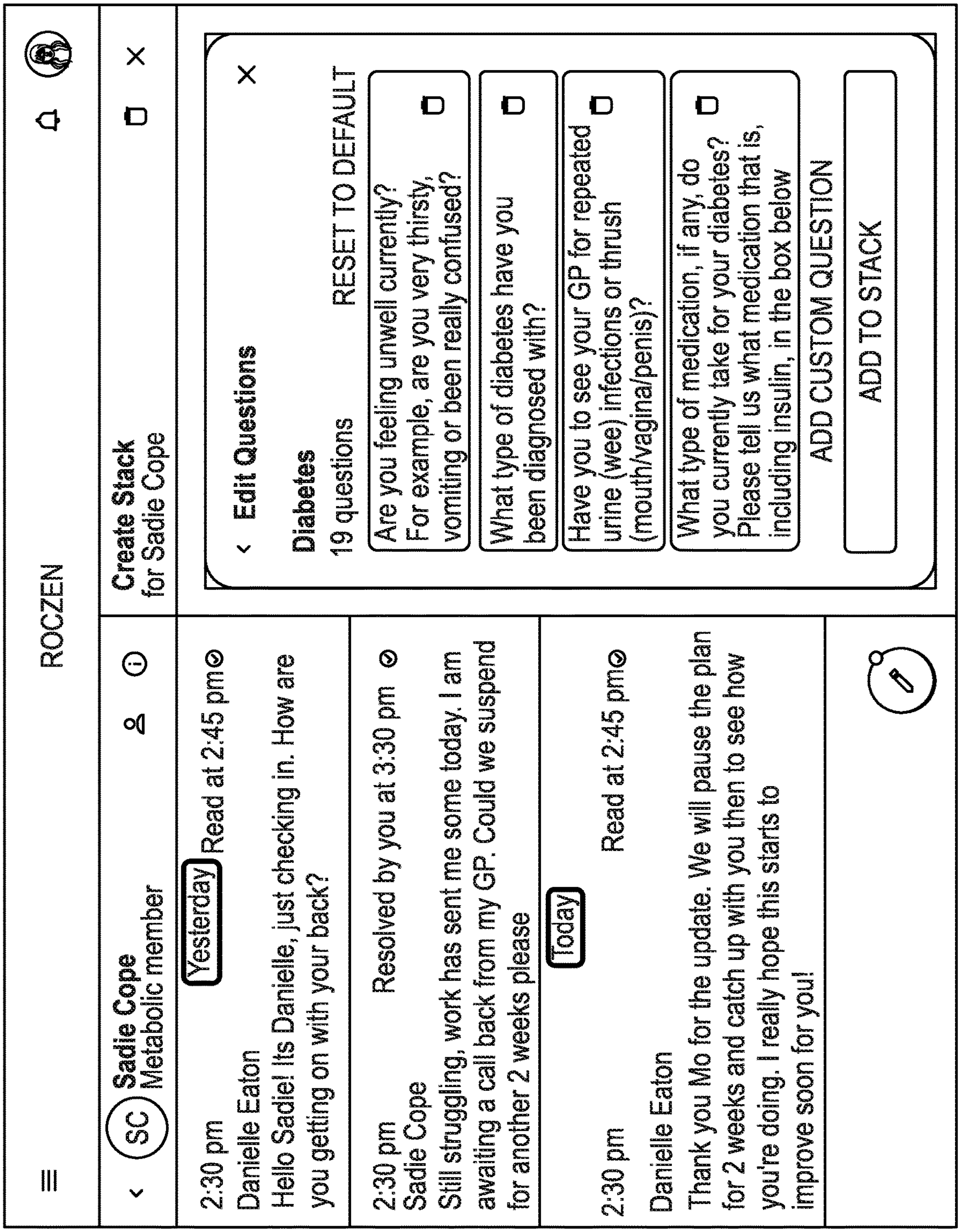
FIG. 5 shows a screen shot of a portion of the system of FIG. 2, including components for editing and customising question cards.

FIG. 5 shows a screenshot of a screen used by a Clinician to edit a template of Questions and customise the questions of a Question Card. The questions shown are example questions only. Different questions may be used. Question Templates may be used to standardise how data is gathered Members. Clinicians can use the templates without any edits or they can remove questions and add custom questions to the Question Card. Once they've edited and added, they can add the bank of Questions to the Stack and send off the Question Card to the Member.

A Stack with a Message and a Question Card can be viewed by a Clinician before being sent to a Member. In this way, Clinicians are shown a summary of exactly what they are sending to the Member as a Stack.

Figure 6:
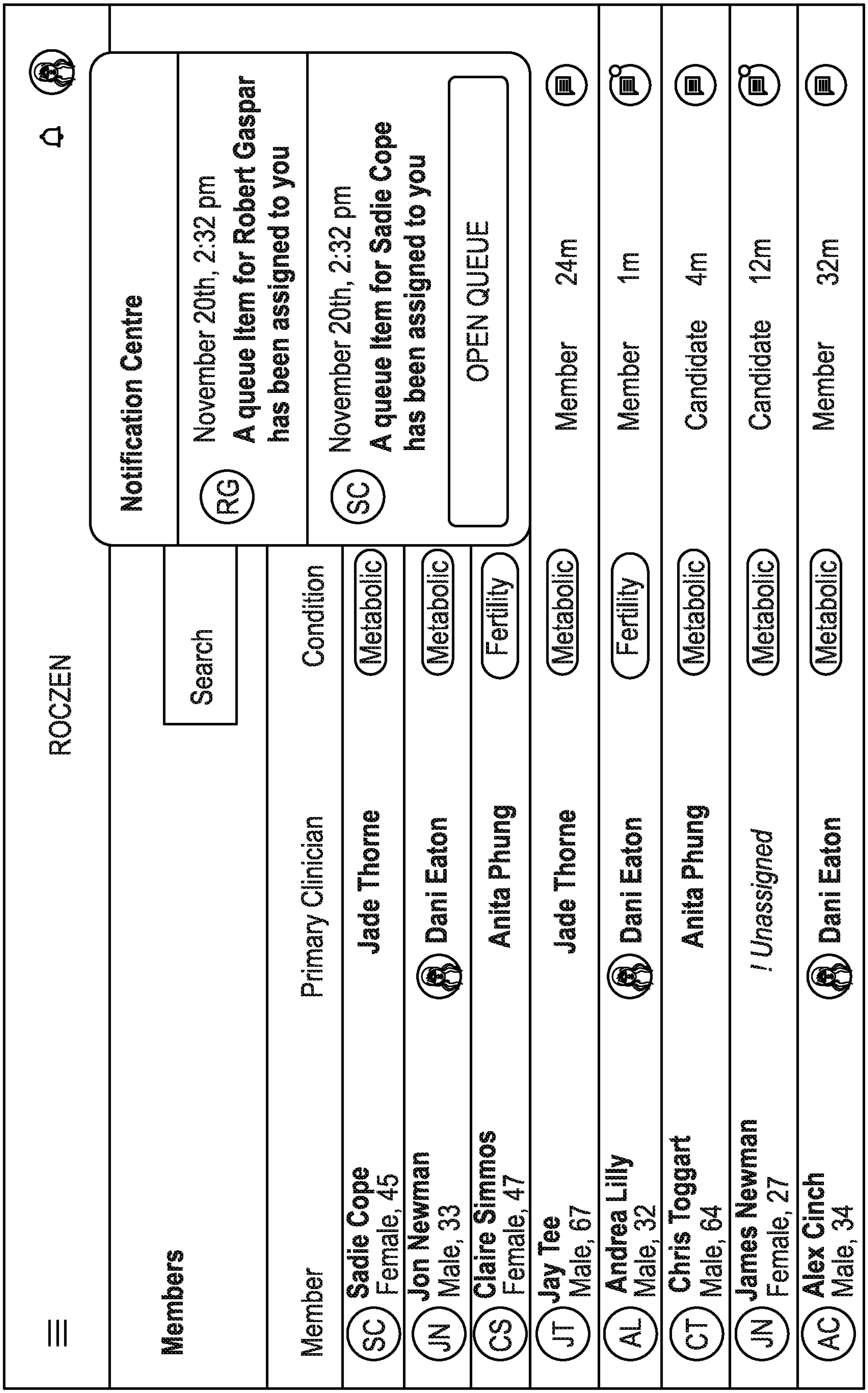
FIG. 6 shows a screen shot of a portion of the system of FIG. 2, including a view of a group of patients.

FIG. 6 shows a screen providing a Clinician with a view of all Members that are included in their Pod and under their care. Clinicians care for a population of Members. The small dot on the message icon indicates that the Member has an action item appearing on the Clinician Queue.

The Clinician Notification Centre is also shown in FIG. 6. As Clinicians send messages and interact with Members within the system, they are provided with a quick view of the latest activity that's landed in the Queue. The Notification Centre allows Clinicians to quickly understand if they need to stop working with one Member to begin working with another Member who has an issue that may be more time sensitive, for example.

A Clinician can view a Member Profile. This allows Clinicians to have a greater understanding of the needs of individual Members and allows Clinicians to edit elements of Member settings and profiles. Similarly, a Clinician can view and edit their own profile. They are able to establish their notification settings, change their password, and carry out other account actions.

Members may create their accounts in different ways. They may find a sponsored account (from a list of employees provided by the client or create their account directly.

Upon logging in to the system, a dashboard shows a Member a list of their channels with a notification showing which channels have new messages or Cards in them. The Dashboard shows Members all of their channels and all of their conditions. The Dashboard includes many other kinds of engagement tools, such as "new recipes added they you may be interested in" and other featured content generated by a Content Management System. A Member Action Centre shows a Member new activity they have across all channels.

Figure 7:
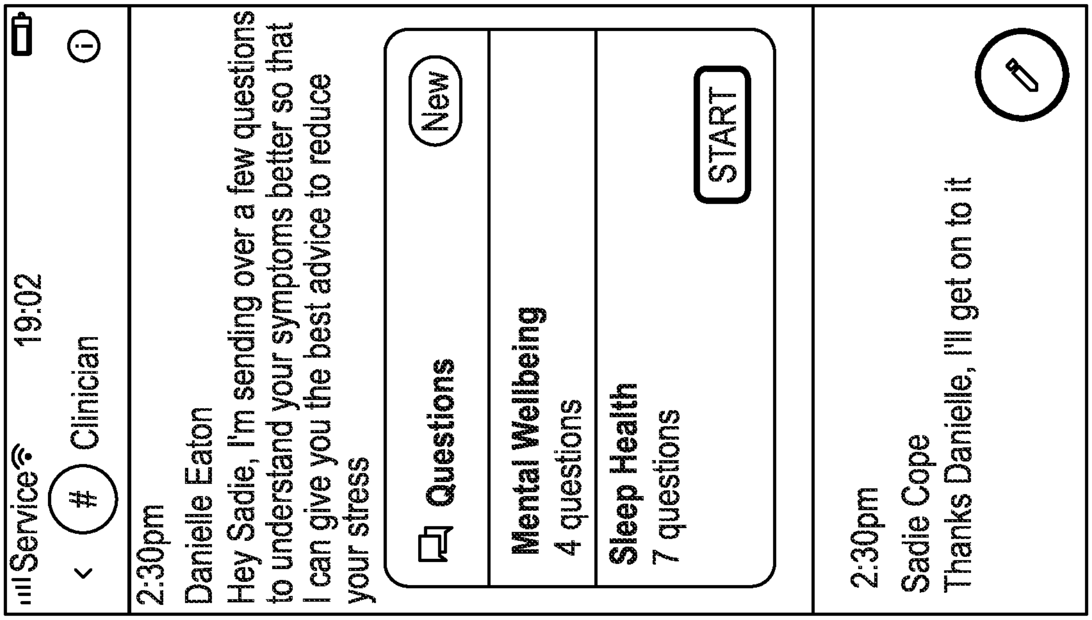
FIG. 7 shows a screen shot of a portion of the system of FIG. 2, including components for patients to view messages and question cards.
Figure 8:
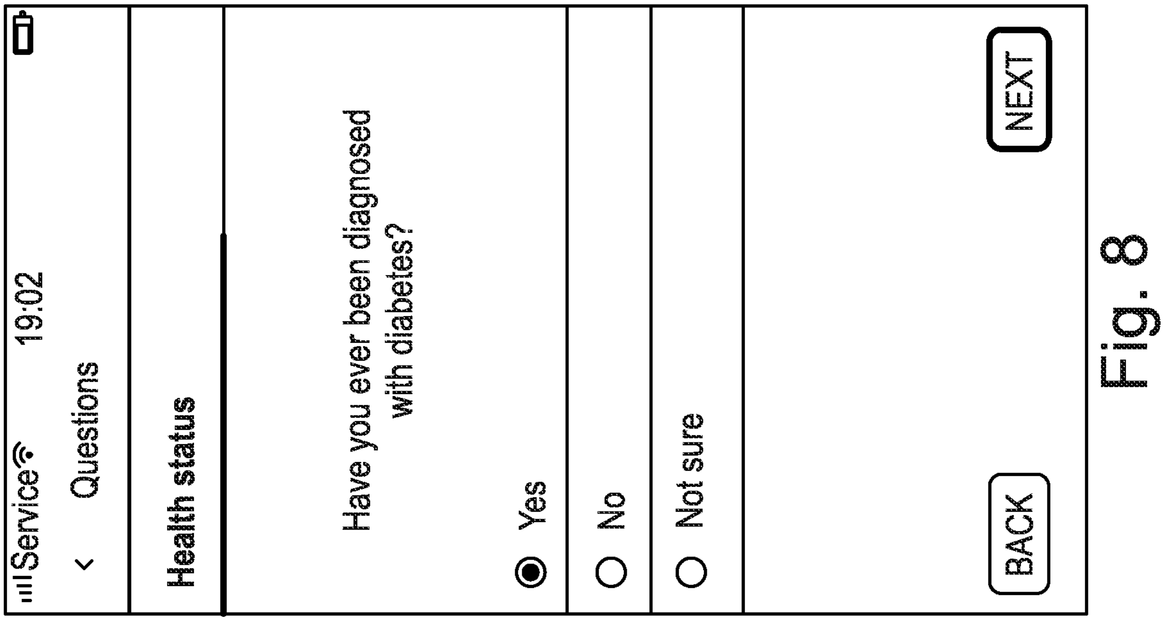
FIG. 8 shows a screen shot of a portion of the system of FIG. 2, including an example question card.

FIG. 7 shows an example screen for a Member. This screen includes their Clinician channel with a message and a Question Card. Clinician Channels may include all messaging and cards that a Member has had with their Clinician team about a specific health condition. Members read new messages and Cards, interact with Cards, and create new messages (responses) to their clinicians.

Cards are interactive and allow more functionality than just messaging with the Members. An example Question Card (or set of queries) is shown as a screen shot in FIG. 8. Cards can have multiple steps, like answering a series of questions found within a card (showing the progress bar above), prior to the Member submitting their responses. Once the Member hits "submit" on their responses, this sends an alert to the Clinicians and adds the submitted responses to the Clinician Queue as a new action item for the Clinicians to handle. The responses are also added to the data store 10 and associated with the health condition. Members may create ad hoc messages to their Clinicians about a specific condition that is being managed.

Members may view a summary of their channel. A channel includes all communications, all cards, and all clinical data about a specific condition that is being managed. The channel overview provides a summary of all of the important information within that channel, so that Members can easily find and digest the most important information within that channel. The Channel Info also shows a brief overview of their Profile and any incomplete action items in the Channel the Member must act on.

Mentors may provide Members with advice. A Mentor may be allocated to one or more Members. A Mentor channel enables this interaction. For each condition (or groups of conditions), Members have a Clinician Channel and a Mentor Channel. The Mentor channel enables Members to asynchronously message with their Mentor. Members may also view and edit sections of their profile and manage their account. This may include payment facilities. A Member can view their Mentor's Bio and profile. This facilitates a very human interaction. Humans want to know details about who they are working with. Video introductions and photos may be included to help deeper relationships that develop over time. In a similar way, a Member can view their Clinician's Bio and profile. Members can customise their notifications and change elements of their account.

Figure 9:
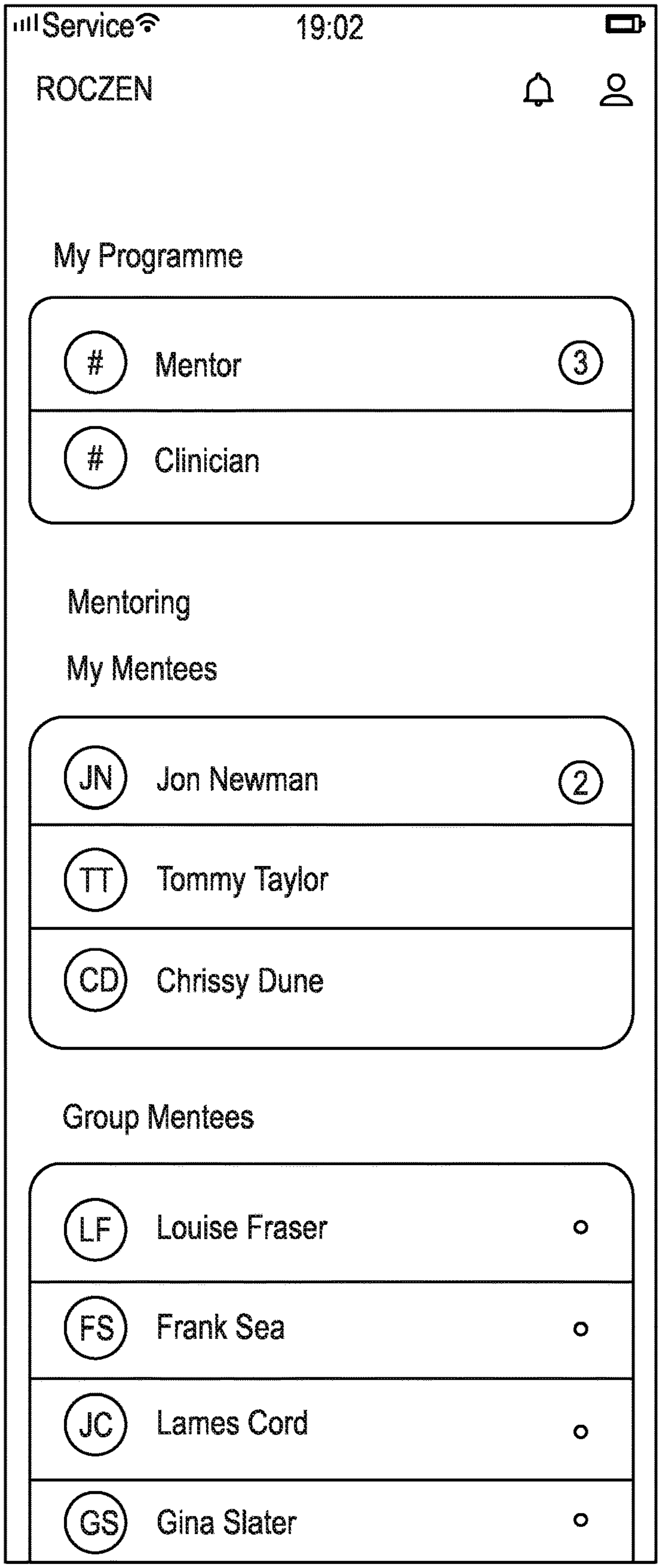
FIG. 9 shows a screen shot of a portion of the system of FIG. 2, including components for displaying a dashboard.

FIG. 9 shows a dashboard of a Mentor. Mentors are also Members. Mentors interact with their Clinician and their Mentors, while also interacting with their Mentees. Mentors have a dashboard to show new activity in their own care and in their Mentees' care. Mentors, like Clinicians, are organised in groups to enable cross-coverage for when Mentors get sick, go on vacation, etc. Mentors can see activity coming from Mentees who are assigned to other Mentors in their Mentor Group. Mentors are provided with a list of all new messages and action items across all channels. Mentor/Mentee Channels house the thread of messages and content about a specific condition.

Mentors may also create ad hoc messages to their Mentees about a specific condition they are managing. Mentors can also view and edit sections of their Mentor profile and manage their account, as it relates to their Mentoring. They can also find the details of other Mentors in their Mentor Group.

Figure 10:
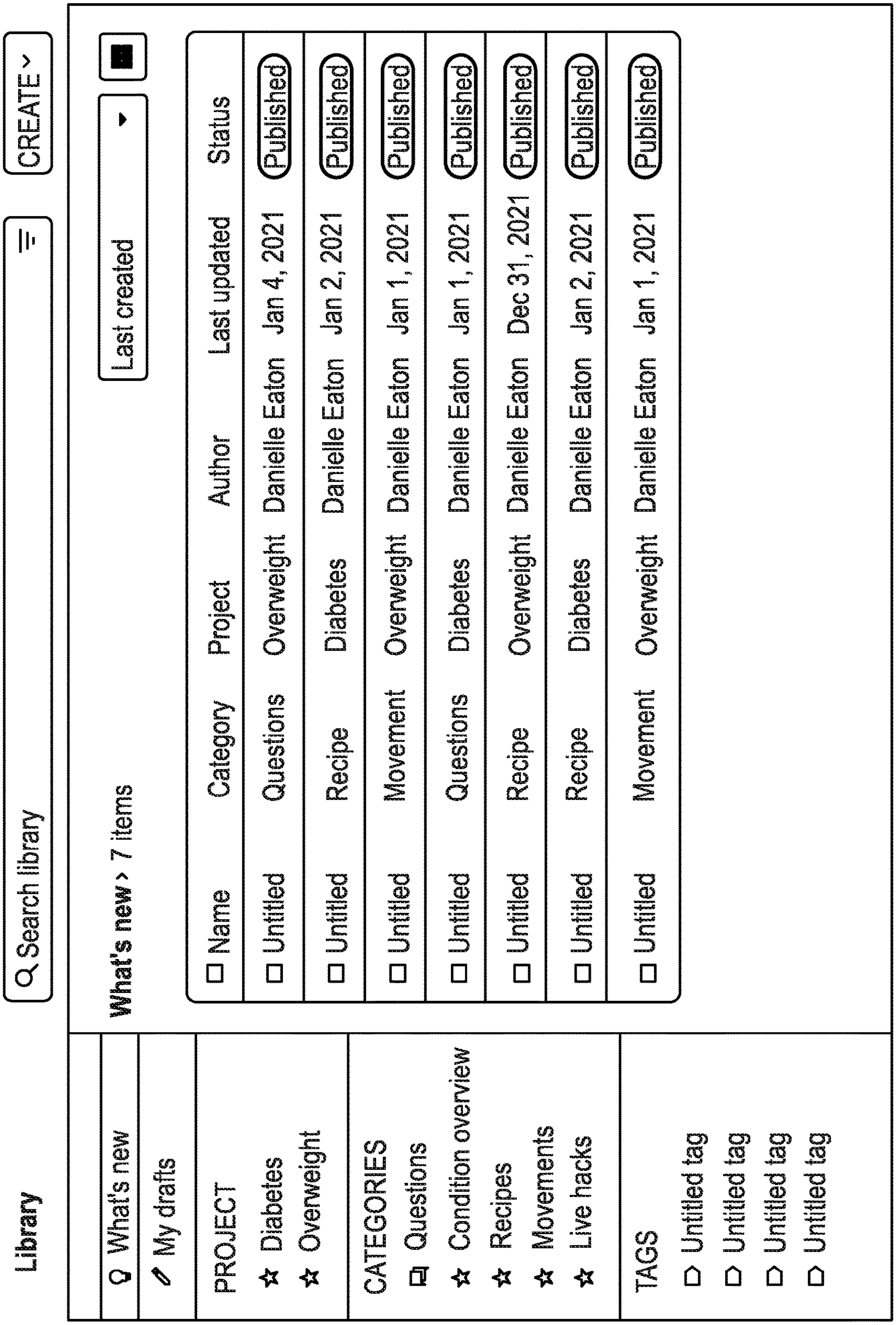
FIG. 10 shows a screen shot of a portion of the system of FIG. 2, including components for viewing a library of system data.

The system 100 includes a Content Management System (e.g., in the form of a Library). FIG. 10 shows an example extract of such a Library. Each item in the Library may be created (e.g., manually or automatically) to help streamline every step of the delivery process and help the Members (i.e., patients) to learn about their condition and change their lifestyle.

Figure 11:
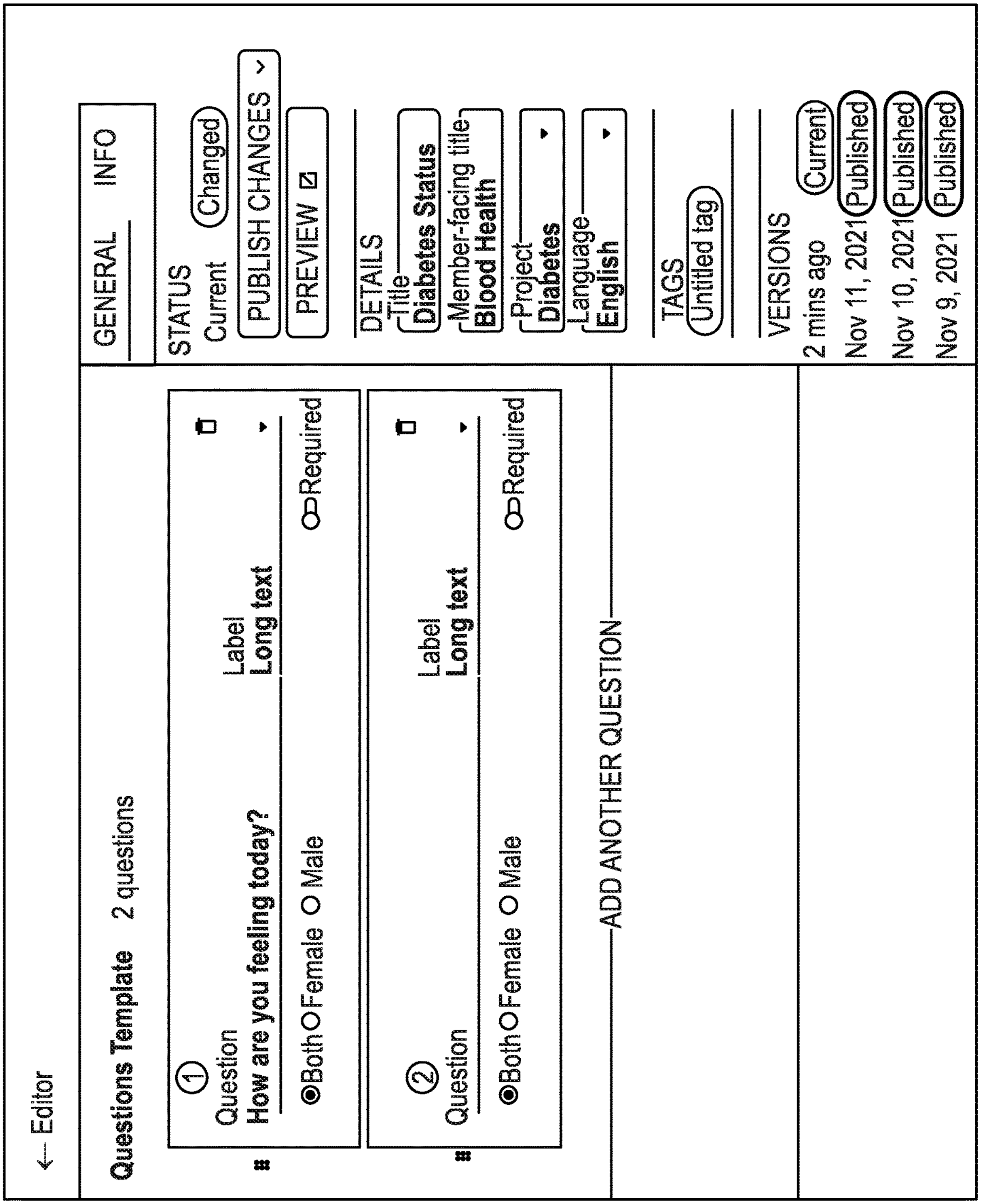
FIG. 11 shows a screen shot of a portion of the system of FIG. 2, including components for editing and customising templates.

FIG. 11 shows a screen for creating a Question Template. About 70% of a doctor's effort is spent collecting information from patients. Automating the collection of information from patients via standardised questionnaires streamlines a doctor's practice. This also allows the system to gather structured data in a scalable way and use that data to constantly improve a delivery model.

The Clinicians can devise queries to be sent to Members. These queries can be stored for later reuse by the same or other Clinicians (e.g., treating the same or similar health conditions). Once responses are collected from one or more Members (patients) having a particular health condition then these responses can be analysed automatically. This analysis can be used to enhance the sets of queries sent to subsequent Members with the same or similar health condition. These subsequent queries can be sent automatically or they can be reviewed by a Clinician.

In one example, if a set of (first) queries included a question regarding the diet of a Member and the response indicated a poor or unbalanced diet then subsequent sets of queries may be sent out to different Members with the same health condition including a query regarding symptoms of a poor or unbalanced diet (e.g., weight, tiredness, sleep problems, etc.) These further queries may be added to subsequent query sets automatically. The automatically generated query sets may be sent out together with or instead of those query sets devised by the Clinicians.

Such further queries may also be added (or changed) based on combinations of responses from separate queries. For example, if some or all of the responses indicated a further health condition that a Member might have (in addition to the primary health condition of current interest) then the new queries added to subsequent query sets for different Members may include queries focused on those different health conditions as well. In this way, the system may also automatically detect Members having health conditions that they are unaware of and so provide early or preventative treatments.

In order to avoid unnecessary communications, should a particular query in a set of queries fail to contribute to understanding or the derivation of a treatment plan or if a particular query often resulted in inconclusive results, then such a query may be removed from subsequent query sets sent to different Members. Again, this may be achieved automatically.

Following the enhancements of query sets, Clinicians do not need to devise new query sets for each Member having a particular health condition as the system 100 can automatically send the Members a current optimum set of queries.

Query sets may be tuned or adjusted in this way for different sets or categories of Members. For example, these may be based on age or gender.

For each condition that a Member has, an estimated treatment period may be calculated. For example, given a particular health condition, received responses (e.g., age, symptoms, etc.) and any other health conditions, the time necessary to reach a particular recovery metric may be calculated. This calculation may also be based on test results. This may be ordered by a Clinician or they may be automatically scheduled by the system 100 based or response and/or test results of previous Members with the same or similar health conditions. As treatment continues, this estimated treatment period may be monitored and updated in response to further queries and responses. These may be directly linked to the particular health condition or may be unrelated, for example. Once the recovery metric has been reached (e.g., target weight, BMI, cessation of symptoms, optimal blood sugar levels, physical flexibility, physiological change, psychological change, memory/alertness improvement, etc.) then the actual recovery period may be stored in the data store 10. This information may be used to update template treatment plans or active treatment plans for other Members. Therefore, data about one or more Members receiving treatment may be used to optimise the treatment or reduce overall treatment time for other Members. Other data may be collected such as recording the effectiveness of particular dose of medications. Again, these data may be used to improve the treatment of future Members.

The process of sending out requests for information to Members, receiving their responses to query sets (one or more queries), generating or updating a treatment plan sent to Members and monitoring the treatment period can iterate or loop until one or more recovery metrics are reached. This process can continue in part or wholly in an automated manner (with or without supervision).

Any and all interactions with Members can become data points and used to enhance further interactions with the same or different Members.

The system 100 collects and stores data from the responses received from Members (patients) and elsewhere. These data are used to improve the performance, reliability, and effectiveness of the system 100. These data sources may include:

Explicit data entered by Members (for example weight, food intake, blood pressure and their written communications).

Implicit data collected by observation of the user (e.g., times that they interact with the service and when they did not, whether or not they responded to treatment plans and communication messages and movement detected via the user's device).

Data from other parties about the Member (e.g., blood test reports and DNA analyses).

Derived data from these sources, e.g., sentiment and other indicators using analysis of their written communication.

The data may be further enhanced from other correlated external sources such as environmental factors like weather, socio-demography based on location, job type, etc.

The data may be continuous (e.g., blood pressure), discrete (e.g., number of pregnancies) or categorical (e.g., vegan), for example.

The provision of health care services requires many years of training and must be applied in a careful and monitored manner. It is particularly important in the treatment of non-communicable chronic diseases (NCD), such as obesity and type 2 diabetes mellitus, which require a care model that involves a prolonged period of treatment that integrate incentives, guidance, mentoring, coaching, ongoing reporting of outcomes resulting in adjustments of the treatment plan to produce the necessary clinical outcome. An important feature of such a care model requires lifestyle and behaviour changes and these can be driven by incentives or rewards, such as social motivation or money.

Some level of automation can be achieved for certain regular tasks, such as the reporting of biometric data (weight and blood pressure) but a high level of manual intervention and monitoring is still required from a health professional, such as a doctor.

Therefore, there is provided a system or sub-system to monitor health mentoring and generate incentives and rewards for health mentors and patients to achieve and maintain a pre-agreed state of health outcomes as (Reset) determined by a medically qualified clinician.

A patient is an individual with an impaired state of health.

A mentor is defined as a patient who has been successfully treated by the care model (e.g., as described above) to reach a defined healthy state (Reset) and then trained and qualified to mentor new patients in this same care model.

(1) The mentor is rewarded for using the system's intelligent data to guide a patient through a clinical treatment plan while at same time allowing the system to monitor and guide both mentor and patient to maintain a healthy state.

(2) The system's algorithm is able to use the ongoing collected health, and other data, from the mentors and patients to monitor and maintain a pre-agreed health status to generate a reward which in turn, would generate health compliance and agreed clinical outcomes for the mentor and the patients.

In this context, mentors augment the clinical care process by supporting Members during their journey on the programme. Whilst Mentors receive training from Reset Health or another entity, they are not clinicians but offer practical experience because they have experienced the programme directly and have themselves improved their health by following the advice and guidance of a clinician and the programme that is devised uniquely for each Member.

Mentoring is a difficult topic to get right, particularly where the mentor/mentee have never met in person. The system supports the Mentors in this job, by helping them optimise their interactions with their Mentees.

The system carries out any one or more of the following tasks:

Tracks how Member are proceeding on their individualised programme, which medium they engage with and when.

Employs machine learning to discover the drivers for each of the individuals involved to try to determine the causal effects of mentoring.

Mentors are given cues by the system about how best to communicate with their Mentees. This includes the time of the day/week the Mentee is most receptive, the medium over which they are most receptive, the types of material they most engage with and similar suggestions.

The system is also capable of analysing the strength of these relationships and recommending to managers (e.g., Reset Health manages) which Mentors are themselves most effective and which can best sustain and nurture more Mentees.

Therefore the feedback loop has been expanded to not only optimise the Clinical Care at an individual basis, but also the Mentoring activities.

Figure 12:
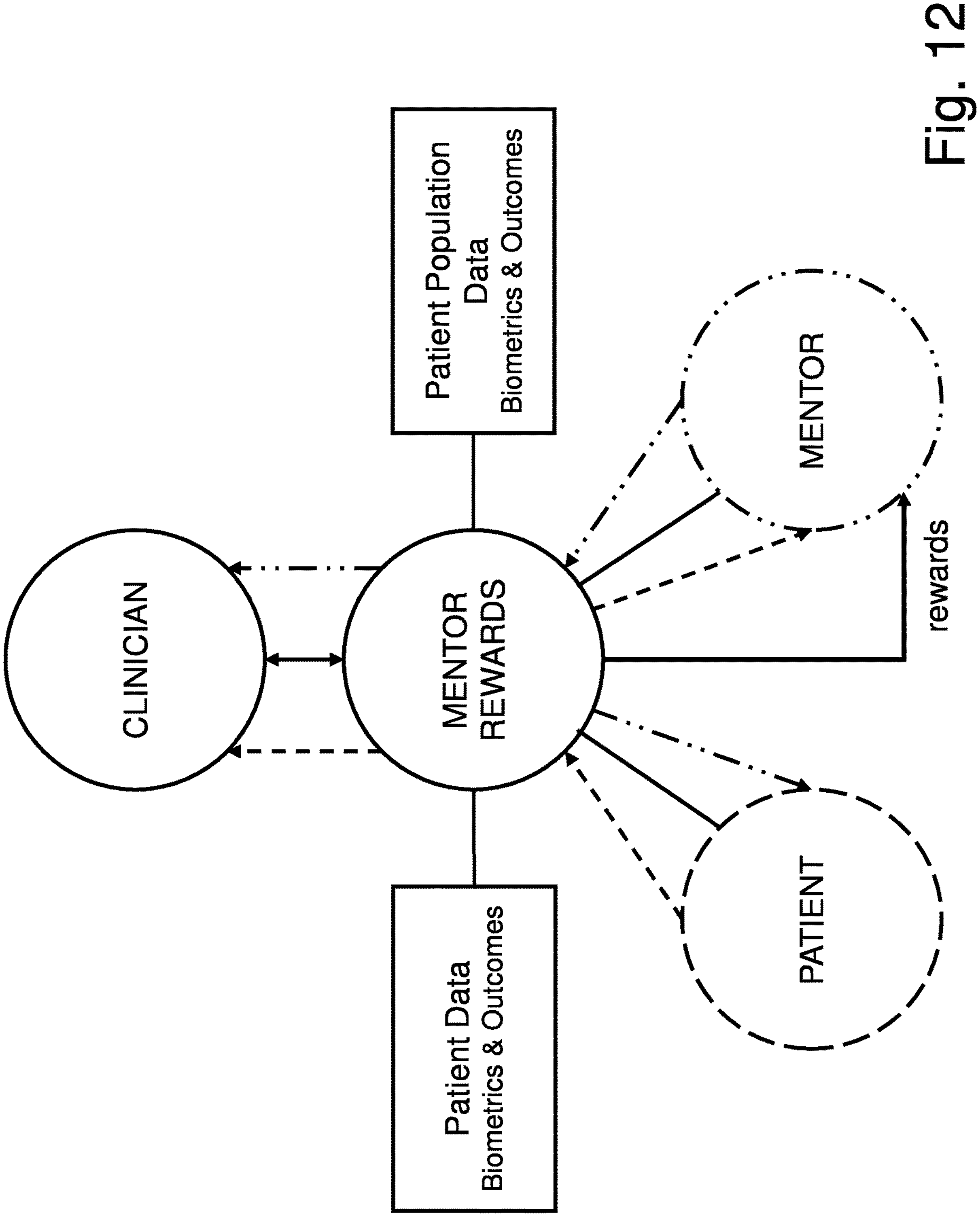
FIG. 12 shows a schematic diagram of an example rewards system used to enhance the method of FIG. 1.

FIG. 12 shows schematically a further enhancement to the method for providing healthcare services. This figure illustrates the interaction between one or more patients, mentors, clinician, and the mentor reward scheme. The patient data includes biometrics and outcomes data. The patient population data also includes biometrics and outcomes data. The outcomes data may be the same data collected using the automated system for providing medical health care services, as described above. As can be seen from FIG. 12, all three types of user (e.g., patient, mentor, and clinician) can receive rewards using this system. This positively encourages behaviour leading to improved health outcomes for patients. The rewards system may be points-based, for example.

As will be appreciated by the skilled person, details of the above embodiment may be varied without departing from the scope of the present invention, as defined by the appended claims.

For example, two user devices have been shown in the figures but any number of user devices (and users or members) may interact with the system. The Clinicians and Mentors may also use similar user devices. More than one processor and/or data store may also be used (e.g., for load balancing purposes or to separate data sets). The data store may be decentralised (e.g., stored in a blockchain).

Many combinations, modifications, or alterations to the features of the above embodiments will be readily apparent to the skilled person and are intended to form part of the invention. Any of the features described specifically relating to one embodiment or example may be used in any other embodiment by making the appropriate changes.

The invention claimed is:

1. A method for improving machine learning classification models and updating patient treatment plans based on updated clusters, the method comprising:

administering, to a first user and based on an original cluster, of a plurality of clusters, assigned to the first user by a trained machine learning model, a first treatment plan for a health condition of the first user;

receiving, from each of a plurality of remote devices corresponding to each of a plurality of second users and after the administering the first treatment plan;

responses to one or more queries and health condition information;

identifying, for each of the plurality of second users, a treatment plan;

recomputing, based on the responses, the health condition information, and the treatment plan for each of the plurality of second users, the trained machine learning model;

identifying, using the recomputed machine learning model and for the first user, a new cluster of the plurality of clusters that corresponds to the first user;

modifying, based on the new cluster, the first treatment plan; and administering, to the first user, the modified first treatment plan.

2. The method of claim 1, wherein the first treatment plan comprises a template treatment plan indicating a first quantity of a prescription medication, and wherein the modified first treatment plan indicates a modified quantity of the prescription medication.

3. The method of claim 1, wherein the modifying the first treatment plan comprises determining that, for one or more users associated with the new cluster, that one or more recovery metrics have not been reached.

4. The method of claim 1, wherein the original cluster corresponds to a first co-relation in a data set, and wherein the new cluster corresponds to an updated co-relation in the data set.

5. The method of claim 1, further comprising:

generating, based on previous responses to previous queries, the one or more queries; and transmitting, to each of the plurality of remote devices, the one or more queries.

6. The method of claim 1, wherein the original cluster corresponds to a first patient outcome, and wherein the new cluster corresponds to an updated patient outcome.

7. The method of claim 1, wherein the trained machine learning model is configured to predict a treatment outcome for the first user.

8. The method of claim 1, wherein the trained machine learning model is trained using training data comprising previous queries, previous responses, and previous treatment plans.

9. The method of claim 1, wherein the modified first treatment plan comprises one or more of:

a medication prescription;

a lifestyle variation;

a diet instruction;

an exercise instruction; or a physiotherapy prescription.

10. The method of claim 1, wherein the modifying, based on the new cluster, the first treatment plan comprises:

generating a medical test plan that comprises one or more medical tests;

administering the one or more medical tests; and modifying the treatment plan further based on results of the one or more medical tests.

11. The method of claim 10, wherein the administering the one or more medical tests comprises administering one or more of:

a blood test;

an X-ray investigation;

an MRI investigation;

a CT scan investigation; or a fitness test.

12. The method of claim 1, further comprising:

receiving, after administering the modified first treatment plan, second responses to one or more second queries; and further modifying the modified first treatment plan based on the second responses to the one or more second queries.

13. The method of claim 1, wherein the health condition of the first user comprises one or more of:

diabetes, heart disease, obesity, or hypertension.

14. The method of claim 1, further comprising:

selecting the one or more queries from a set of queries stored in a data store.

15. The method of claim 14, further comprising:

generating new queries based on the responses; and storing the new queries in the data store.

16. A method for improving machine learning classification models and updating patient treatment plans based on updated clusters, the method comprising:

computing, based on a history of past queries, past responses to the past queries, past treatment plans, and indications of efficacy, a trained machine learning model;

administering, to a first user and based on an original cluster, of a plurality of clusters, assigned to the first user by the trained machine learning model, a first treatment plan for a health condition of the first user;

recomputing, after administering the first treatment plan and based on second responses to second queries, the trained machine learning model;

identifying, using the recomputed machine learning model and for the first user, a new cluster of the plurality of clusters that corresponds to the first user;

modifying, based on the new cluster, the first treatment plan; and administering, to the first user, the modified first treatment plan.

17. The method of claim 16, wherein the first treatment plan comprises a template treatment plan indicating a first quantity of a prescription medication, and wherein the modified first treatment plan indicates a modified quantity of the prescription medication.

18. The method of claim 16, wherein the modifying the first treatment plan comprises determining that, for one or more users associated with the new cluster, that one or more recovery metrics have not been reached.

19. The method of claim 16, wherein the original cluster corresponds to a first co-relation in a data set, and wherein the new cluster corresponds to an updated co-relation in the data set.

20. The method of claim 16, wherein computing the trained machine learning model comprises computing the trained machine learning model using an artificial intelligence component of a processor.

* * * * *